United States Patent
Rask

(10) Patent No.: US 11,324,394 B2
(45) Date of Patent: May 10, 2022

(54) ENDOSCOPE

(71) Applicant: AMBU A/S, Ballerup (DK)

(72) Inventor: Jesper Domino Rask, Copenhagen (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/361,102

(22) Filed: Jun. 28, 2021

(65) Prior Publication Data

US 2022/0079417 A1  Mar. 17, 2022

(30) Foreign Application Priority Data

Sep. 20, 2020  (DK) .......................... PA 2020 70593

(51) Int. Cl.
*A61B 1/005*  (2006.01)
*A61B 1/00*  (2006.01)
*A61B 1/05*  (2006.01)

(52) U.S. Cl.
CPC ........ *A61B 1/0052* (2013.01); *A61B 1/00048* (2013.01); *A61B 1/0057* (2013.01); *A61B 1/00114* (2013.01); *A61B 1/05* (2013.01)

(58) Field of Classification Search
CPC ..... A61B 1/0052; A61B 1/005; A61B 1/0051; A61B 1/0057; A61B 2017/003; A61B 2017/00318; A61B 2017/00323; A61B 2017/00327
USPC ................ 600/103, 106, 118, 131, 139–142, 600/146–150; 604/528
See application file for complete search history.

(56) References Cited

U.S. PATENT DOCUMENTS

| | | | |
|---|---|---|---|
| 9,220,400 B2 | 12/2015 | Petersen | |
| 9,968,241 B2 | 5/2018 | Iuel | |
| 10,321,804 B2 | 6/2019 | Jacobsen et al. | |
| 10,624,531 B2 | 4/2020 | Matthison-Hansen | |
| 10,624,617 B2 | 4/2020 | Matthison-Hansen et al. | |

(Continued)

FOREIGN PATENT DOCUMENTS

| | | |
|---|---|---|
| JP | H 6304126 | 11/1997 |
| JP | 2005279120 A | 10/2005 |

(Continued)

OTHER PUBLICATIONS

First Technical Examination Report issued in Danish application No. PA 2020 70593, dated Feb. 2, 2021, 9 pages.

(Continued)

*Primary Examiner* — Ryan N Henderson
*Assistant Examiner* — Pamela F Wu
(74) *Attorney, Agent, or Firm* — Faegre Drinker Biddle & Reath LLP

(57) ABSTRACT

An endoscope including a handle including a fulcrum with a fulcrum axis, and a control lever including a lever body attached to the fulcrum and rotatable about the fulcrum axis, a lever grip, and a lever arm attaching the lever grip to the lever body, the control lever being adjustable between a first and a second configuration, in which the gripping surface of the lever grip is distanced from the fulcrum axis at a first radial distance via the lever body and lever arm, and a second configuration, in which the gripping surface of the lever grip is distanced from the fulcrum axis at a second radial distance via the lever body and lever arm, wherein the second radial distance is different from the first radial distance.

16 Claims, 9 Drawing Sheets

(56) References Cited

U.S. PATENT DOCUMENTS

| | | |
|---|---|---|
| 10,964,844 B2 | 3/2021 | Lutgen |
| 2005/0003103 A1 | 1/2005 | Krupa |
| 2007/0270644 A1 | 11/2007 | Goldfarb et al. |
| 2011/0166420 A1 | 7/2011 | Miesner et al. |
| 2011/0306831 A1 | 12/2011 | Kohnke et al. |
| 2012/0041533 A1 | 2/2012 | Bertolino et al. |
| 2013/0041214 A1 | 2/2013 | Maahs et al. |
| 2014/0088497 A1 | 3/2014 | Campbell |
| 2017/0042411 A1 | 2/2017 | Kang et al. |
| 2017/0280793 A1 | 10/2017 | Hatano |
| 2018/0049625 A1* | 2/2018 | Nakade ............. A61B 1/00071 |
| 2018/0207403 A1 | 7/2018 | Wang |
| 2019/0053690 A1 | 2/2019 | Suzuki et al. |
| 2019/0254503 A1 | 8/2019 | Hatano et al. |
| 2019/0350440 A1 | 11/2019 | Leong et al. |

FOREIGN PATENT DOCUMENTS

| | | |
|---|---|---|
| JP | 2016067620 A | 5/2016 |
| WO | WO2014/106511 A1 | 7/2014 |

OTHER PUBLICATIONS

Second Technical Examination issued in Danish application No. PA 2020 70593, dated May 20, 2021, 3 pages.
Third Technical Examination/Intent to Grant, issued in Danish application No. PA 2020 70593, dated May 28, 2021, 2 pages.
Intent to Grant for related divisional application, issued in Danish application No. PA 2021 70203, dated Jun. 24, 2021, 7 pages.
Extended search report in related European Application No. 21196569.4 dated Feb. 1, 2022, 9 pages.

* cited by examiner

ENDOSCOPE

CROSS-REFERENCE TO RELATED APPLICATIONS

This application claims the benefit of and priority from Danish Patent Application No. PA 2020 70593, filed Sep. 15, 2020, which is incorporated herein by reference in its entirety.

TECHNICAL FIELD

The present disclosure relates to an endoscope with a length-adjustable control lever, a kit of parts with such a control lever as well as an endoscope system comprising such an endoscope.

BACKGROUND

Insertion endoscopes are well known devices in the medical field for visually examining the interior of a hollow organ or cavity of a body, such as lungs or a bladder or intestines, by means of inserting an insertion portion of the endoscope. The insertion portion of the endoscope comprises an elongated insertion tube, a distal tip part, and a bending section connecting the insertion tube with the distal tip part. The endoscope typically has a handle connected to the insertion tube and positioned at the proximal end as seen from the operator. The endoscope further has a vision device, such as a built-in camera or fibre optics. The vision device is typically incorporated in the distal tip part at the distal end of the endoscope. This definition of proximal as being closest to an operator and distal as being furthest from an operator is used throughout this disclosure. Illumination of the area in front of the distal tip part of the endoscope is normally required, in particular the field of vision of the vision device. One known way of achieving such illumination is to incorporate one or more Light Emitting Diodes (LEDs) in the distal tip part of the endoscope, e.g. as mentioned in WO2014/106511 disclosing a disposable endoscope. Alternatively, illumination may be provided by light guides and/or fibre optics for guiding light from a light source outside the endoscope and to the distal tip part.

The bending section is provided in order to manoeuvre the endoscope inside the body cavity. The bending section has increased flexibility, e.g. achieved by a number of articulated segments of which the distal tip part forms the distalmost segment. Bending or straightening of the bending section in the insertion part of the endoscope is typically done by tensioning or slacking, respectively, steering wires running from the distal tip part through the remainder of articulated segments and along the inside of the elongated insertion tube to a control mechanism, such as a control lever, of the handle.

Data and/or power cables for the vision device (when being a camera) and other electronics, such as LED lighting accommodated in the distal tip part, also run along the inside of the elongated insertion tube and the bending section from the handle to the distal tip part. Furthermore, a working channel may further run along the inside of the insertion tube and the bending section from the handle to the distal tip part, e.g. allowing liquid to be removed from the body cavity or allowing the insertion of medical tools or surgical instruments into the body cavity.

However, manoeuvring the endoscope while a tool is inserted through the working channel may sometimes be difficult as the tool increases the stiffness of the bending section which in turn makes the control lever hard to operate.

Further, as such an endoscope is typically made to accommodate an average hand size, operators with larger or smaller hands may have difficulty operating the handle in the intended way.

SUMMARY

In light of the above, it may be seen as an object of the present disclosure to provide an endoscope handle with an improved control lever.

One or more of these objects may be met by aspects of the present disclosure as described in the following.

A first aspect of this disclosure relates to an endoscope for visually inspecting inaccessible places such as human body cavities, the endoscope comprising an insertion tube extending to a bending section having with a distal end fixed to a distal tip part including a camera connected with one or more data and/or power cables running through the bending section and insertion tube, and at least one steering wire connected with the distal end of the bending section and operable to cause bending of the bending section, the endoscope having a handle comprising:
  a fulcrum with a fulcrum axis, and
  a control lever including a lever body attached to the fulcrum and rotatable about the fulcrum axis, a lever grip having a gripping surface configured for frictionally engaging a finger of an operator, and a lever arm attaching the lever grip to the lever body, the lever body being configured to be connected with the at least one steering wire so that rotation of the control lever about the fulcrum causes tensioning of the at least one steering wire to effect bending of the bending section, the control lever being adjustable between a first and a second configuration,
wherein:
  in the first configuration, the gripping surface of the lever grip is distanced from the fulcrum axis at a first radial distance via the lever body and lever arm, and
  in the second configuration, the gripping surface of the lever grip is distanced from the fulcrum axis at a second radial distance via the lever body and lever arm, wherein the second radial distance is different from the first radial distance.

This allows the operator to adapt the length of the lever arm of the control lever (i.e. the radial distance from the fulcrum axis) so as to adapt the position of the gripping surface to the operator's hand size or length or finger length. In case an increased force is needed when bending the bending section, e.g. when a tool is inserted through the working channel, the operator can decide to increase the length of the lever arm. By increasing the length of the control lever's arm, the operator can apply an increased moment on the control lever when operating the control lever to bend the distal end of the insertion tube during the relevant procedure. Thereby the operator will provide the required bending without applying excessive force when operating the control lever. This greatly enhances the working conditions for the operator and may increase operator's ergonomics/comfort during endoscopic procedures, e.g. urology procedures, or gastrointestinal procedures.

In particular, the configuration with larger radial distance from the fulcrum axis allows an operator to reach a higher torque with the same input force since the radial distance is comparably longer in the second configuration than in the first configuration. This higher torque may be especially useful, e.g. when the endoscope comprises a working channel and a tool is inserted through a portion of the working channel running through the bending section, as this increases the stiffness of the bending section. The other configuration may further improve the operability of the control lever by an operator with smaller hands and thus smaller thumb reach since the radius of the rotation arc of the lever grip is smaller when using the configuration with the lowest radial distance from the fulcrum axis.

Additionally or alternatively, the lever body may be configured for receiving the lever arm. The control lever may comprise a first guide member, a first engagement member, and preferably a second engagement member. The guide member may form part of either the lever body or the lever arm, and the engagement member(s) may form part of the other one of the lever body and the lever arm. The engagement member(s) may be configured for engaging with the first guide member so that, when the lever body receives the lever arm in the first configuration, the first engagement member is in engagement with the guide member to position the gripping surface of the lever grip at the first radial distance from the fulcrum axis, and preferably so that, when the lever body receives the lever arm in the second configuration, the second engagement member is in engagement with the guide member to position the gripping surface of the lever grip at the second radial distance from the fulcrum axis. This allows for a particular simple way of inserting the lever arm into the lever body to provide an adjustable control lever.

Additionally, the lever arm may be detachable from the lever body.

Additionally, the guide member may be a groove, preferably forming part of the lever body, and the engagement member(s) may be one or a pair of protrusions, preferably forming part of the lever arm, configured to be inserted into the groove. The engagement members may preferably be positioned on opposite sides of the lever arm. The groove may comprise a stop configured for engaging the engagement members to prevent the lever arm from being inserted further into the groove. Alternatively, the guide member may be a protrusion and the engagement member(s) may be groove(s). Hereby is obtained that the operator can easily insert the lever arm into the lever body by matching the engagement member(s) with the corresponding guide member.

Additionally or alternatively, the lever arm may longitudinally extend along its longitudinal axis. The longitudinal axis being perpendicular to the fulcrum axis, and the lever arm being rotatable about the longitudinal axis and the lever arm being configured so that rotation of the lever arm about its longitudinal axis causes the control lever to move between the first configuration and the second configuration. This may be achieved by the lever arm comprising a screw thread and the lever body comprising a corresponding screw thread.

Additionally or alternatively, the lever arm may be fixed to the lever body, optionally via a snap fit.

Additionally or alternatively, the control lever may be configured so that rotation of the lever arm about its longitudinal axis in a first direction causes the control lever to move from the first configuration to the second configuration. Additionally or alternatively, the control lever may be configured so that rotation of the lever arm about its longitudinal axis in a second direction opposite to the first direction causes the control lever to move from the second configuration to the first configuration.

Additionally or alternatively, a 180-degree rotation of the lever arm about its longitudinal axis in the first direction causes the control lever to move from the first to the second configuration. Additionally or alternatively, a 180-degree rotation of the lever arm about its longitudinal axis in the second direction causes the control lever to move from the second to the first configuration.

Additionally or alternatively, the lever arm of the control lever may be telescopically extendable so that a radial force relative to the fulcrum axis on the lever grip causes the control lever to move between the first configuration and the second configuration.

Additionally or alternatively, the control lever may comprise a locking mechanism, optionally a fixing snap fit, configured for preventing the lever arm from being removed from the lever body.

Additionally or alternatively, the gripping surface of the lever grip may be textured. A textured gripping surface may increase the friction to ease the operation of the control lever.

Additionally or alternatively, the endoscope may be a disposable endoscope which may not be intended to be cleaned and/or sterilised for reuse.

Additionally or alternatively, the endoscope may further comprise:
  a bending section having a proximal end and a distal end fixed to the distal tip part,
  an insertion tube extending from the endoscope handle to the proximal end of the bending section,
  a distal tip part including a camera,
  one or more cables running through the bending section and insertion tube and connecting the camera with the endoscope handle, and
  at least one steering wire connecting the lever body with the distal end of the bending section so that rotation of control lever about the fulcrum axis cause bending of the bending section.

A second aspect of this disclosure relates to a kit of parts for an endoscope for visually inspecting inaccessible places such as human body cavities, the kit of parts comprising:
  an endoscope including a handle comprising a fulcrum with a fulcrum axis, and a lever body attached to the fulcrum and rotatable about the fulcrum axis, the lever body being configured to be connected with at least one steering wire of the endoscope and being configured for receiving a lever arm,
  a first lever part comprising a first lever grip having a first gripping surface configured for frictionally engaging a finger of an operator, and a first lever arm configured for attaching the first lever grip to the lever body of the endoscope handle to form a first control lever, wherein rotation of the first lever grip of the first control lever about the fulcrum causes a tensioning force on the at least one steering wire to effect bending of the bending section, and
  a second lever part comprising a second lever grip having a second gripping surface configured for frictionally engaging a finger of an operator, and a second lever arm configured for attaching the second lever grip to the lever body of the endoscope handle to form a second control lever, wherein rotation of the second lever grip of the second control lever about the fulcrum causes a tensioning force on the at least one steering wire to effect bending of the bending section,
wherein the first and second lever parts are exchangeable so that the first gripping surface of the first control lever is positioned at a first radial distance from the fulcrum axis when the first lever arm is attached to the lever body, and the second gripping surface of the second control lever is positioned at a second radial distance from the fulcrum axis when the second lever arm is attached to the lever body, the second distance being different from the first distance.

Additionally or alternatively, the first lever arm and/or the second lever arm may be configured to be detachable from the lever body of the control lever. This allows the operator to switch between the first and second lever arm and use the one suitable for the desired purpose.

Additionally or alternatively, the first lever arm and/or the second lever arm may be configured to attach to and/or detach from the lever body via a snap fit. This allows quick reconfiguration of the control lever.

Additionally or alternatively, the endoscope handle may comprise a locking mechanism having a lock state, a release state, and a locking member. In the lock state, the locking member is engaged with the first lever arm or second lever arm to prevent detachment of the first lever arm or second lever arm. In the release state, the locking member is disengaged from the first lever arm or second lever arm to enable removal of the first lever arm or second lever arm from the lever body.

Additionally or alternatively, the locking mechanism may be biased towards the lock state when the first lever arm or the second lever arm is received by the lever body, the locking mechanism comprising an actuator, which is configured for bringing the locking mechanism from the lock state to the release state when the actuator is actuated by the operator.

Such a locking mechanism may be implemented in the following way. A lever arm comprising two snap-fit cantilevers configured to attach to and detach from the lever body (see FIG. 8 and associated description) and further a central hole extending from the gripping surface and terminating between the two snap-fit cantilevers, and a lock pin positioned in the central hole and being spring-biased to be wedged between snap-fit cantilevers to bring the lever arm in the lock state. An operator can thus pull the lock pin overcoming the spring-bias to withdrawn the lock pin from being wedged between the snap-fit cantilevers to allow the snap-fit cantilevers to bend backwards towards the longitudinal axis of the lever arm to allow the operator to pull the lever arm out from the lever body. Other ways of achieving such locking function is known to the skilled person.

Additionally or alternatively, the endoscope may further comprise:
  a bending section having a proximal end and a distal end fixed to the distal tip part,
  an insertion tube attaching the endoscope handle to the proximal end of the bending section,
  a distal tip part including a camera, and
  at least one steering wire connecting the body lever with the distal end of the bending section so that rotation of control lever about the fulcrum cause bending of the bending section.

Additionally or alternatively, the endoscope may comprise one or more data and/or power cables running along the bending section and insertion tube and connecting the camera with the endoscope handle.

A third aspect of this disclosure relates to an endoscope system for visually inspecting inaccessible places, such as human body cavities, the endoscope system comprising an endoscope according to the first aspect or a kit of parts according to the second aspect of this disclosure, and a monitor, wherein the endoscope is connectable to the monitor via one or more cables or via a wireless connection, e.g. a standard radiofrequency wireless connections such as Bluetooth, Wi-Fi, etc. The monitor is configured for displaying an image captured by the camera of the endoscope.

A fourth aspect of this disclosure relates to a method of adjusting a length of a control lever of an endoscope handle, the method comprising the steps of providing an endoscope according to the first aspect, and adjusting the control lever so as to move the control lever between the first and second configuration.

Additionally or alternatively, the step of adjusting the control lever may be performed by rotating the control lever of its longitudinal axis, e.g. by an angle in the first direction to move the control lever from the first configuration to the second configuration, or an angle in the second direction to move the control lever from the second to the first direction. The angle may be 180 degrees.

Additionally or alternatively, the step of adjusting the control lever may be performed by telescopically extending the lever arm of the control lever to move the control lever between the first configuration and the second configuration.

A fifth aspect of this disclosure relates to a method of adjusting a length of a control lever of an endoscope, the method comprising the steps of providing a kit of parts according to the second aspect of this disclosure, choosing either the first lever part or the second lever part, and attaching the chosen lever part to the lever body of the handle. The method may further comprise a step of detaching the chosen lever part and attaching the other lever part to the lever body of the handle thereby exchanging lever parts.

A person skilled in the art will appreciate that any one or more of the above aspects of this disclosure and embodiments thereof may be combined with any one or more of the other aspects of this disclosure and embodiments thereof.

BRIEF DESCRIPTION OF THE DRAWINGS

Embodiments of this disclosure will be described in more detail in the following with regard to the accompanying figures. The figures show one way of implementing the present invention and are not to be construed as being limiting to other possible embodiments falling within the scope of the attached claim set.

DETAILED DESCRIPTION

Figure 1:
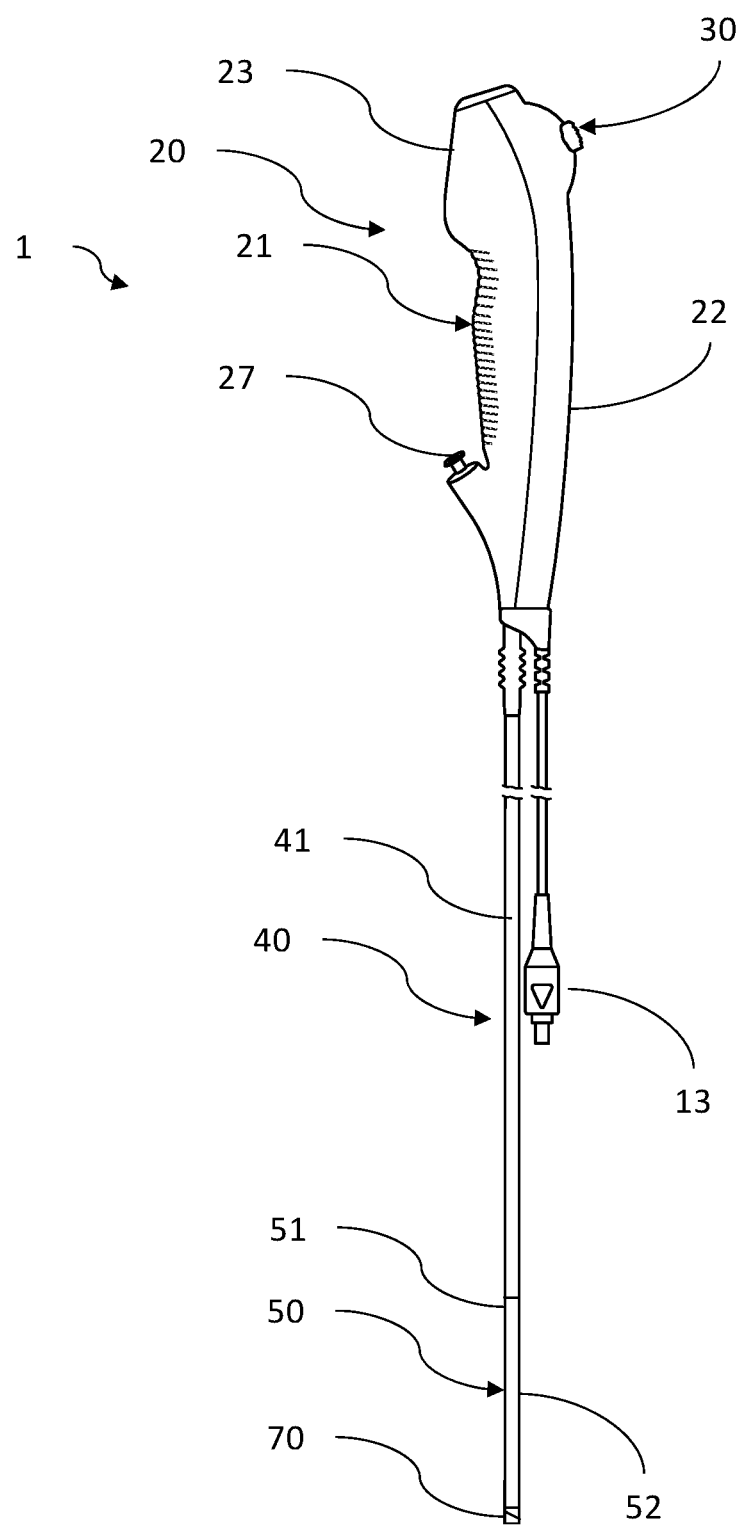
FIG. 1 is a schematic perspective illustration of an endoscope according to this disclosure.

FIG. 1 illustrates an endoscope 1, which is disposable and not intended to be cleaned and reused. The endoscope 1 comprises a distal tip part 70, a handle 20 with a handle housing 21 for gripping and a control lever 30, an insertion tube 40 for insertion into a patient and extending between the handle 20 and a proximal end 51 of a bending section 50, and a camera (not shown) positioned in the distal tip part 70. The handle housing 21 comprises a top housing half 22 and a bottom housing half 23. The insertion tube 40 has an exterior tubular surface 41 facing the surroundings of the endoscope 1. The camera is in signal communication with a circuit (not shown) of the handle 20 via data and power cables (not shown). The bending section 50 comprises articulated segments (not shown), hinges (not shown) connecting the segments, and a thin outer sleeve 52 covering the segments and hinges and providing an additional layer of sealing for the connection between the distal tip part 70 and the bending section 50. The thin outer sleeve 52 also provides a smooth outer surface for the bending section 50 in order to improve the comfort of a patient undergoing endoscopy. Furthermore, a working channel (not shown) may run along the inside of the insertion tube from a working channel opening 27 of the handle 20 to the distal tip part 70, e.g. allowing liquid or air to be added to and/or removed from the body cavity or allowing the insertion of medical tools or surgical instruments into the body cavity.

Figure 2:
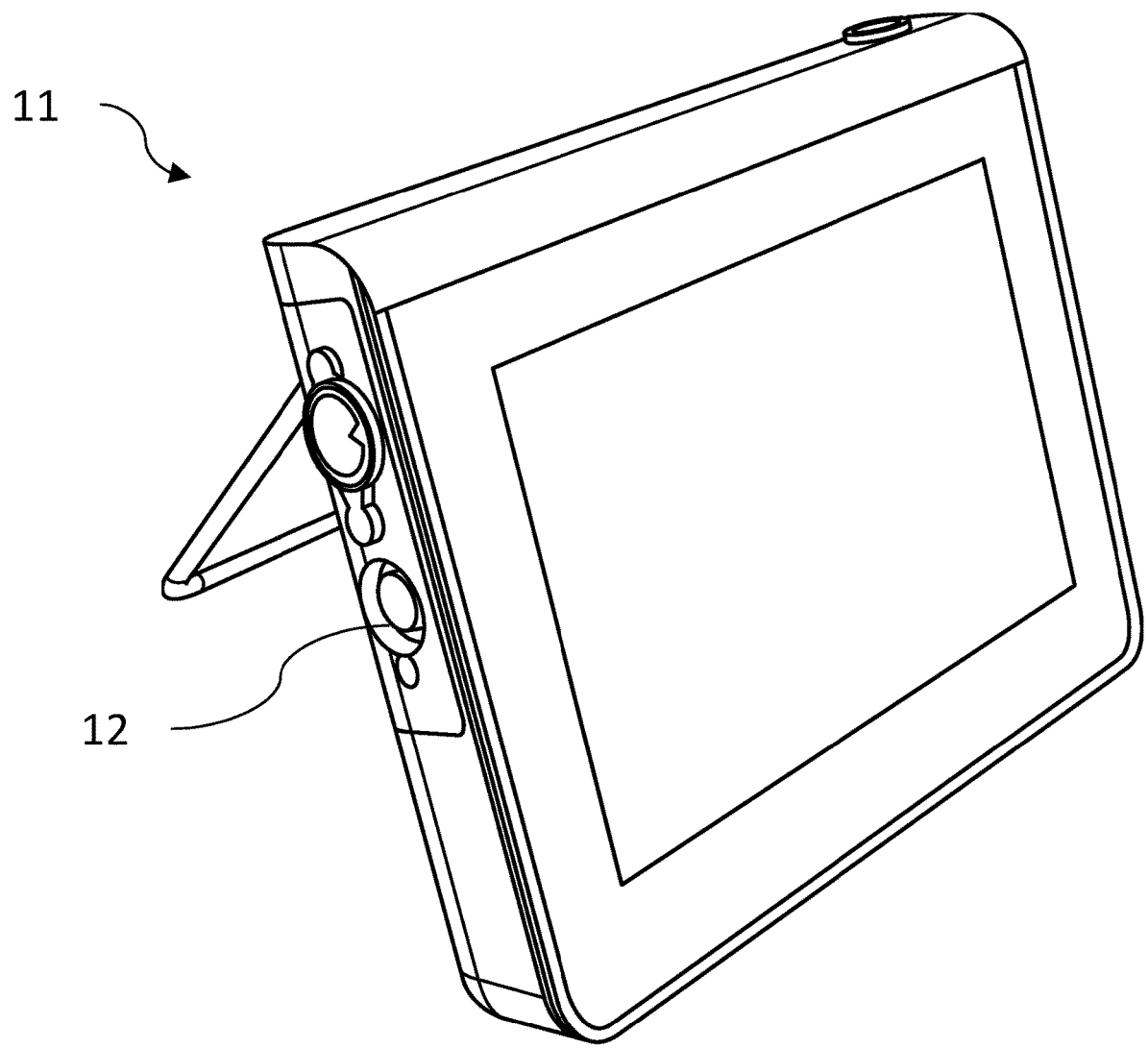
FIG. 2 is a schematic perspective illustration of a monitor connectable to the endoscope.

In FIG. 2, a monitor 11 is shown. The monitor 11 comprises a cable socket 12 to which a monitor cable 13 of the endoscope 1 (shown in FIG. 1) can be connected to establish signal communication between the camera of the endoscope 1 and the monitor 11 via the circuit. The monitor 11 display images and/or video captured by the camera of the endoscope 1 thus allowing an operator to "see" the body cavity through the camera of the endoscope 1.

Figure 3:
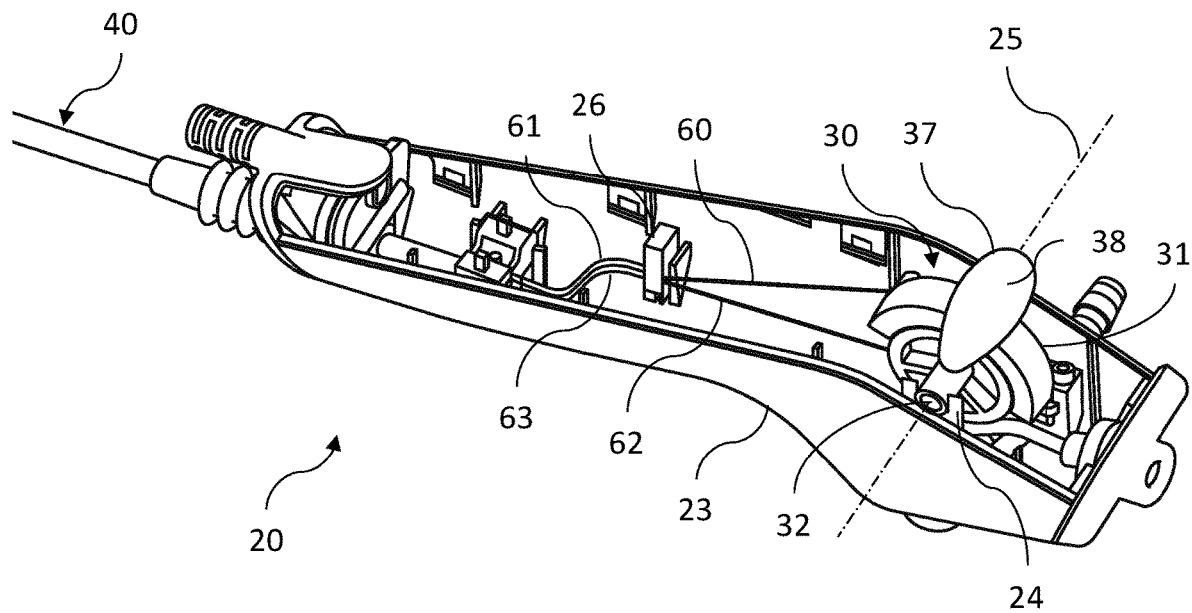
FIG. 3 is a schematic perspective illustration of the interior of an endoscope handle.

FIG. 3 illustrates a handle 20 wherein the top housing half 22 is removed to reveal the interior of the handle 20. The handle 20 comprises a fulcrum 24 with a fulcrum axis 25. The control lever 30 comprises a lever grip 37, a lever body 31, and a lever arm 34 extending along its longitudinal axis 34a which is perpendicular to the fulcrum axis 25. The lever grip 37 and lever arm 34 are described in more detail in connection with FIGS. 5 and 7. The lever body 31 is in the form of a roller and comprises a shaft 32 supported by the fulcrum 24 and rotatable about the fulcrum axis 25. First and second steering wires 60, 62 are fixed at one end to the lever body 31 spaced apart on opposite sides of the fulcrum axis 25 (see FIG. 3 wherein the first steering wire 60 is fixed on the lever body 31 "above" the fulcrum axis 25 and the second steering wire 62 is fixed on the lever body 31 "below" the fulcrum axis 25) and at the other end to a distalmost segment (not shown) of the bending section 50 and run through a fixed sheath 61, 63, respectively. The fixed sheaths 61, 63 are fixed to and terminate in a block 26 of the handle 20. By manipulation of the lever grip 37, the control lever 30 rotates about the fulcrum axis 25 to tension one of the steering wires 60, 62 relative to the respective sheath 61, 63, thereby functioning as a Bowden cable to effect bending of the bending section 50.

Figure 4:
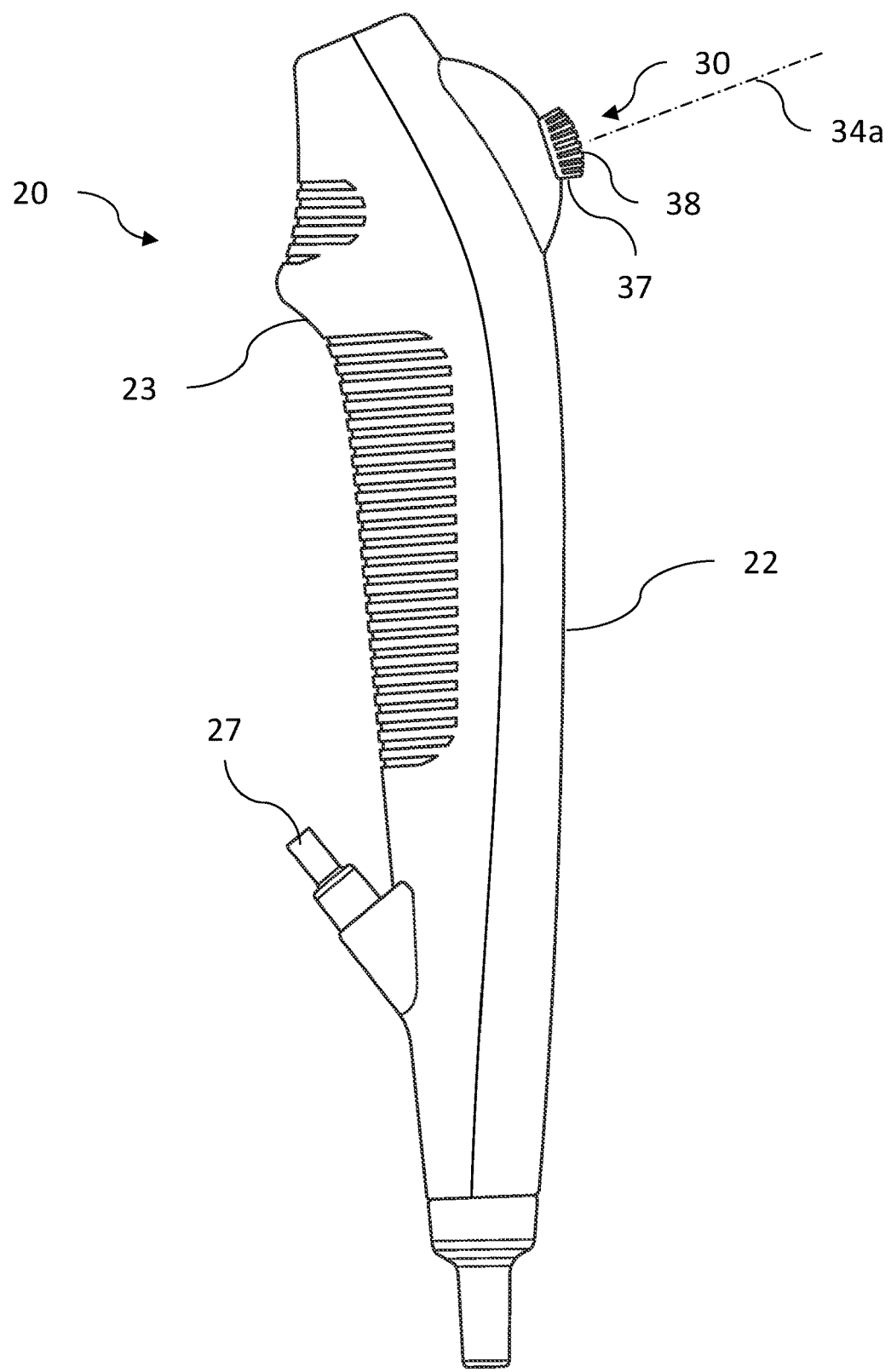
FIG. 4 is a schematic perspective illustration of an endoscope handle in a first configuration.
Figure 5:
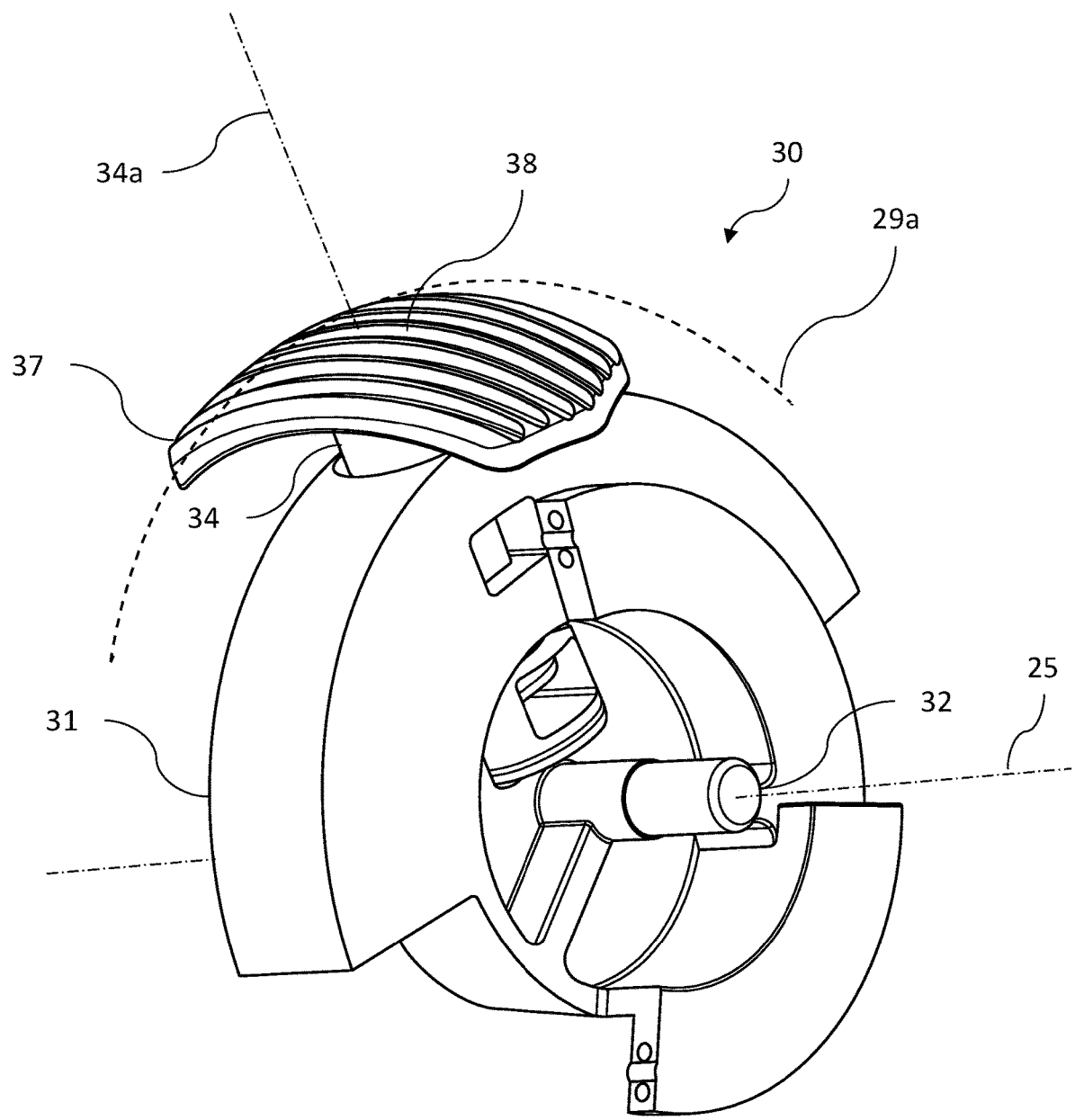
FIG. 5 is a schematic perspective illustration of a control lever in the first configuration.
Figure 6:
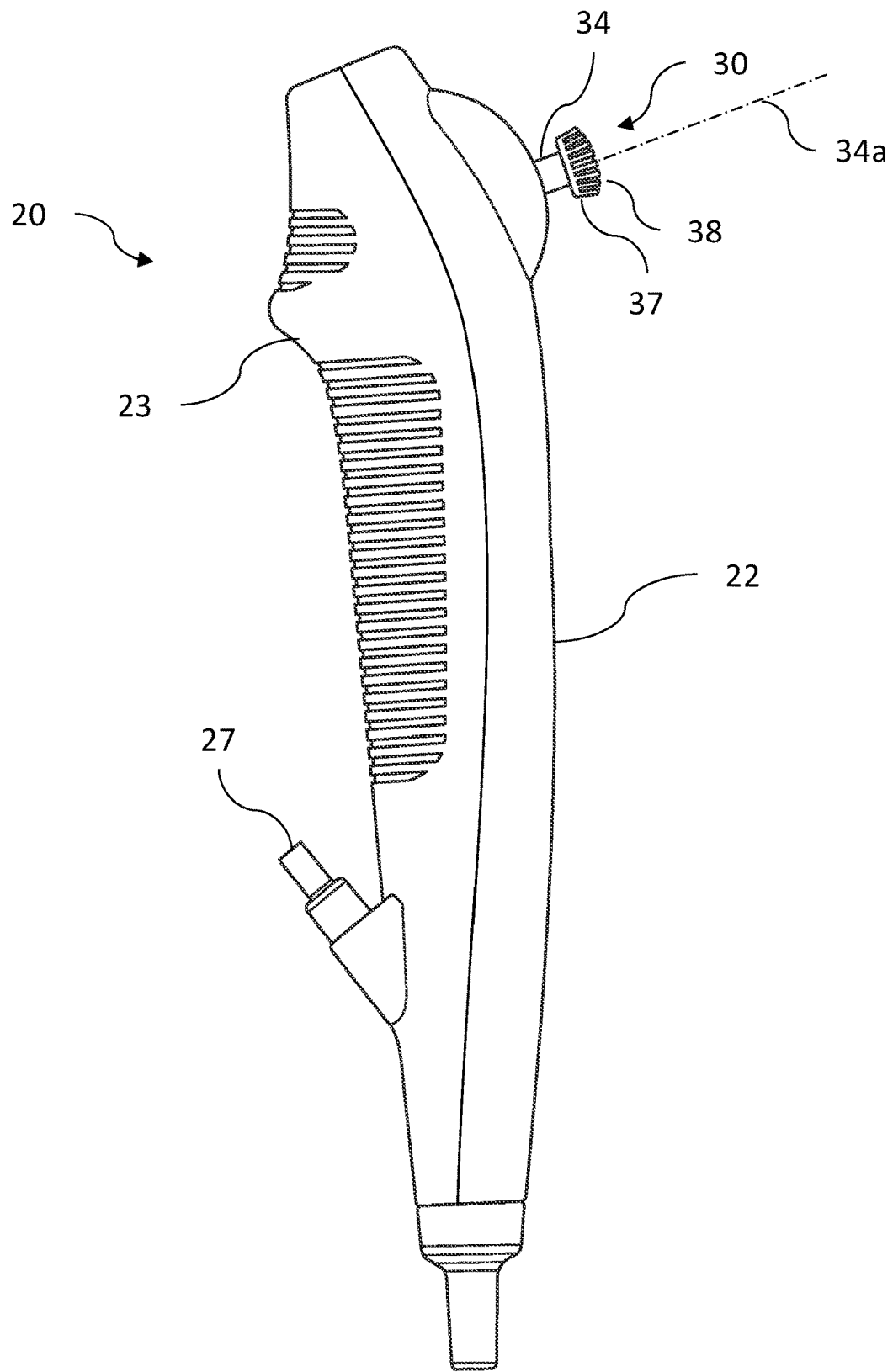
FIG. 6 is a schematic perspective illustration of an endoscope handle in a second configuration.
Figure 7:
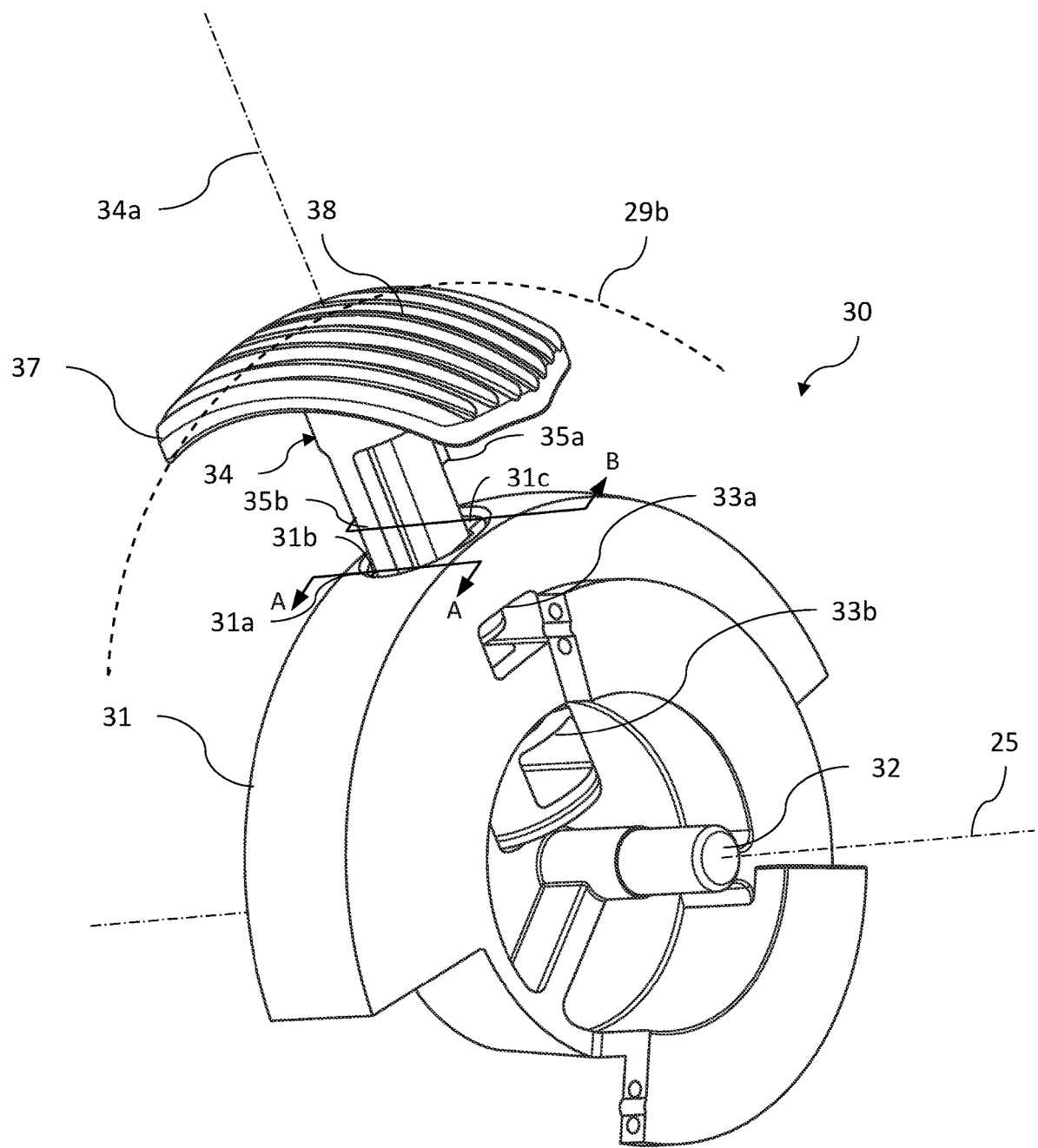
FIG. 7 is a schematic perspective illustration of the control lever in the second configuration.

The control lever 30 is adjustable between a first configuration and a second extended configuration. In the first configuration as shown in FIGS. 4-5, the gripping surface 38 of the lever grip 37 is distanced from the fulcrum axis 25 at a first radial distance 29a via the lever body 31 and lever arm 34 as best seen in FIG. 5. In the second extended configuration as shown in FIGS. 6-7, the gripping surface 38 of the lever grip 37 is distanced from the fulcrum axis 25 at a second radial distance 29b via the lever body 31 and lever arm 34 as best seen in FIG. 7. The second radial distance 29b is different from the first radial distance 29a by about 20 mm, in particular the first radial distance 29a is e.g. about 50 mm while the second radial distance 29b is about 70 mm. The second configuration allows an operator to reach a higher torque with the same input force since the radial distance is comparably longer in the second configuration than in the first configuration. This higher torque is useful, e.g. when a tool is inserted through a portion of the working channel running through the bending section, as this increases the stiffness of the bending section. The first configuration further improves the operability of the control lever 30 by an operator with smaller hands and thus smaller thumb reach since the radius of the rotation arc of the lever grip 37 is smaller in the first configuration relative to the second configuration.

Figure 8:
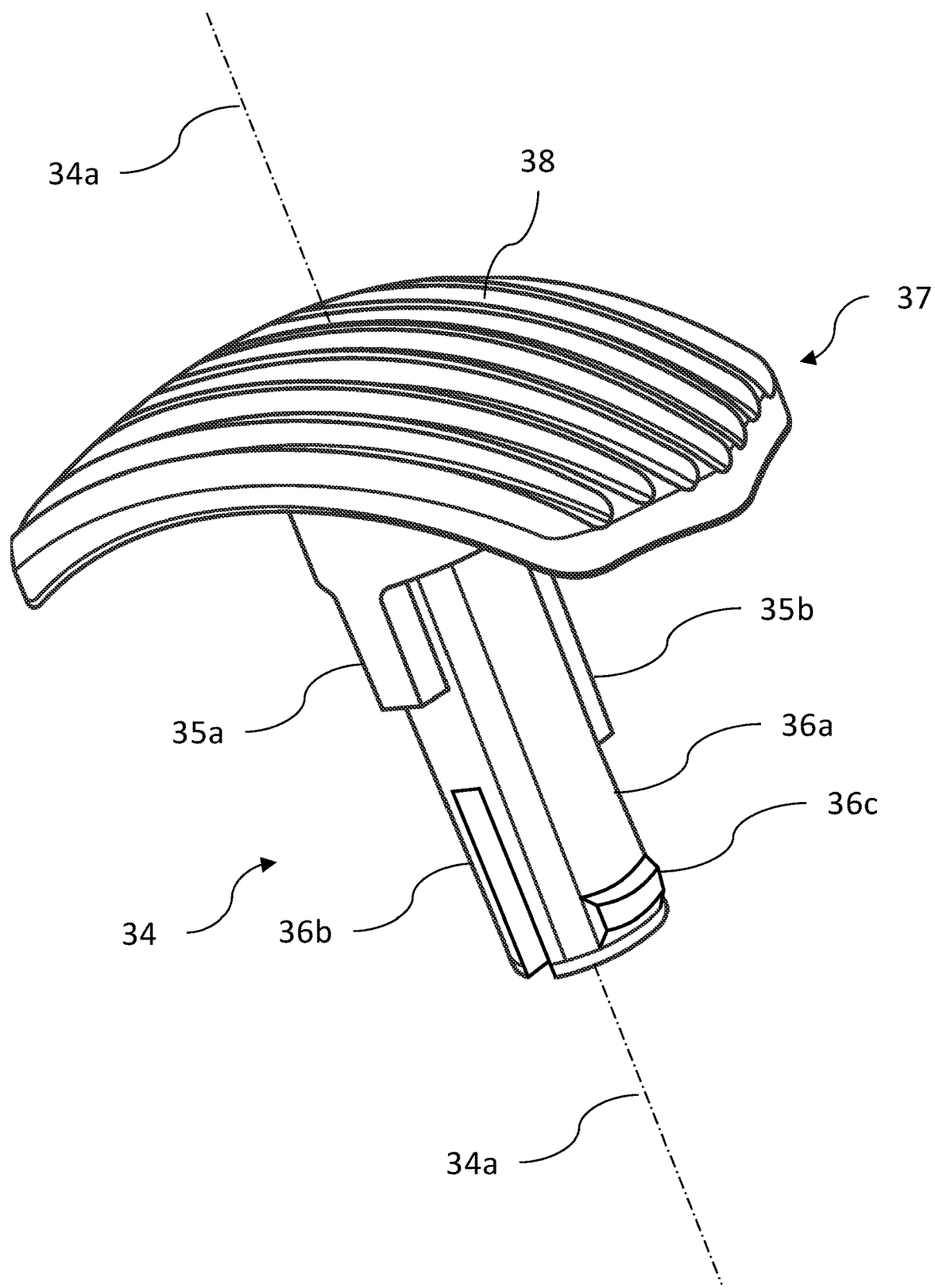
FIG. 8 is a schematic perspective illustration of a lever arm and lever grip of the control lever.

Turning to FIGS. 7-8, the lever arm 34 of the present embodiment extends along its longitudinal axis 34a and comprises a first engagement member 35a and a second longer engagement member 35b in the form of ridges extending along longitudinal axis 34a on opposite sides of the lever arm 34. It should be understood that, as used in this application, the terms first and second are only used to distinguish different elements and are thus interchangeable. As best seen in FIG. 7, the lever body 31 comprises an opening 31a including a first guide 31b and a second guide 31c in the form of guide channels extending along the longitudinal axis 34a of the lever arm 34 on opposite sides of the opening 31a. The guides 31b, 31c are configured to receive the engagement members 35a, 35b so that the lever arm 34 can be inserted into the opening 31a in two different orientations, first orientation, and a second orientation in which the lever arm 34 is rotated 180 degrees about the longitudinal axis 34a. Each guide 31b, 31c comprises a stop 31d, 31e (shown in FIGS. 9 and 10) to prevent the lever arm 34 from being inserted further once one of the engagement members 35a, 35b engages the corresponding stop. The longer engagement member 35b contacts the first or second stop 31d, 31e to determine the first radial distance 29a and the second radial distance 29b.

As best seen in FIG. 8, the end of the lever arm 34 opposite the lever grip 37 comprises two snap-fit cantilevers 36a, 36b, each with a snap fit protrusion 36c having sloped sides along the longitudinal axis 34a of the lever arm 34. Turning back to FIG. 7, the lever body 31 comprises an upper snap-fit ledge 33a and a lower snap-fit ledge 33b. When the lever arm 34 is inserted into the opening 31a of the lever body 31 in a first orientation about the longitudinal axis, the second engagement member 35b, which is longer than the first engagement member 35a, enters the corresponding first guide 31b. Once the end of the lever arm 34 reaches the upper snap-fit ledge 33a, the protrusion 36c of each of the snap-fit cantilevers 36a, 36b snaps into engagement with the upper snap-fit ledge 33a to lock the control lever 30 in the second configuration as shown in FIGS. 6-7. If the lever arm 34 is pushed further along its longitudinal axis 34a, the snap-fit cantilevers 36a, 36b snap out of engagement with the upper snap-fit ledge 33a due to the sloped sides of the protrusion 36c until the first engagement member 35a engages the stop of the first guide 31b, preventing further insertion of the lever arm 34 and the protrusion 36c of each snap-fit cantilever 36a, 36b snaps into engagement with the lower snap-fit ledge 33b to lock the control lever 30 in the first configuration as shown in FIGS. 4-5.

The lever arm 34 and lever grip 37 can then be detached from the lever body 31 by pulling on the lever grip 37 along its longitudinal axis 34a until the protrusion 36c snaps out of engagement with the lower snap-fit ledge 33b and afterwards out of engagement with the upper snap-fit ledge 33a. Reoriented by rotating 180 degrees about the longitudinal axis 34a and reinserted into the opening 31a, the second longer engagement member 35b then enters the second guide 31c and engages a stop preventing further insertion of the lever arm 34. At this location, the protrusion 35c snaps into engagement with the upper ledge 33a to lock the lever arm 34 and lever grip 37 in the second configuration as shown in FIGS. 6-7.

Figure 9:
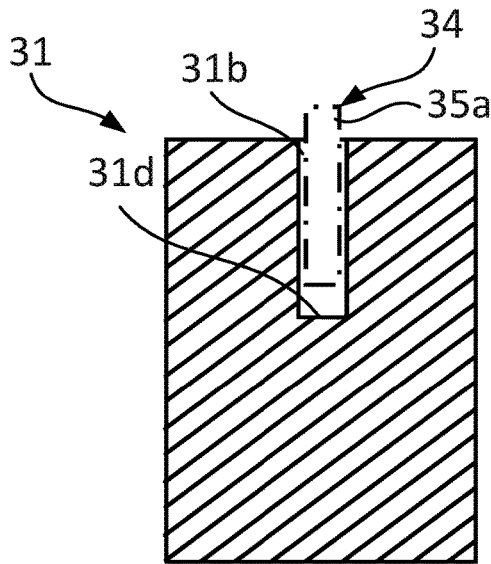
FIGS. 9 and 10 are partial cross-sectional views of the lever body showing first and second guide channels extending longitudinally and radially outwardly from a surface of an elongate opening according to the embodiment depicted in FIG. 8, and FIGS. 11 and 12 are partial cross-sectional views of the lever body showing first and second longitudinal ridges extending longitudinally and radially inwardly from a surface of the elongate opening.
Figure 10:
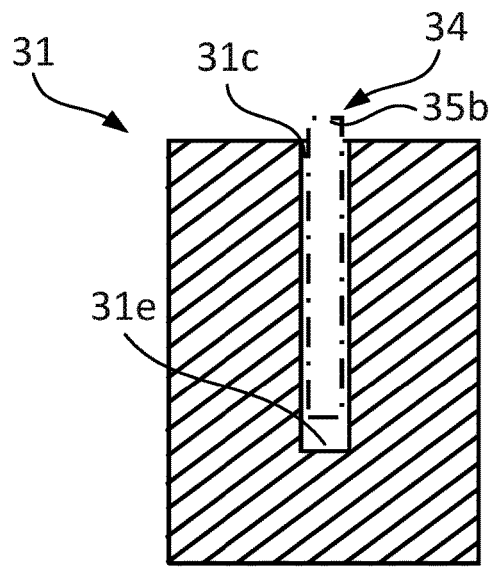
Figure 11:
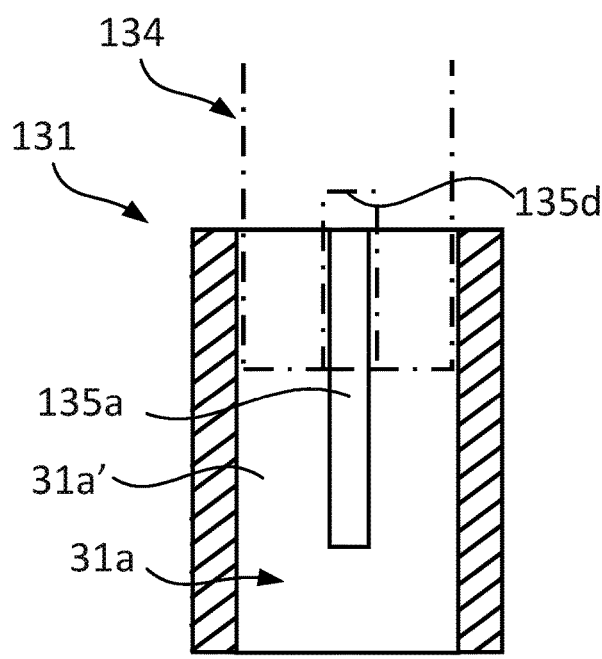
Figure 12:
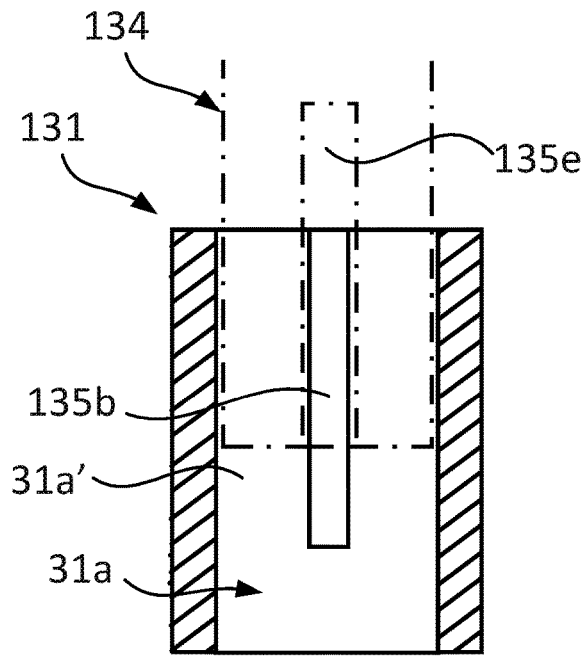

As mentioned below with reference to item 1, the lever body is configured for receiving the lever arm, wherein the control lever comprises a first guide member, a first engagement member, and preferably a second engagement member, wherein the guide member forms part of either the lever body or the lever arm and the engagement member(s) form part of the other one of the lever body and the lever arm, the engagement member(s) being configured for engaging with the first guide member so that, when the lever body receives the lever arm in the first configuration, the first engagement member is in engagement with the guide member to position the gripping surface of the lever grip at the first radial distance from the fulcrum axis, and preferably so that, when the lever body receives the lever arm in the second configuration, the second engagement member is in engagement with the guide member to position the gripping surface of the lever grip at the second radial distance from the fulcrum axis. The opening 31a is provided in the lever body and sized and shaped to receive the lever arm. The guide members, or guide channels, can be provided in either the lever body or the lever arm. Matching engagement members, or longitudinal ridges, can be provided, respectively, in the lever body or the lever arm. As used herein longitudinal refers to a direction along the length of the elongate opening. FIGS. 9 and 10 are partial cross-section views along lines A-A and B-B, shown in FIG. 7, illustrating the guide channels 31b, 31c and corresponsing stops 31d, 31e at the bottom of each channel to prevent the lever arm 34 from being inserted further. The longer engagement member 35b contacts the first stop 31d to determine the second radial distance 29b. FIGS. 11 and 12 are partial cross-section views of the embodiment in which the guide channels 135a, 135b are provided in the lever arm 134 and ridges 135a, 135b are provided in the lever body 131. To show the engagement members the sectional views are taken closer to the longitudinal axis of the opening 31a than sections A-A and B-B, resulting in a portion of the surface of opening 31a, denoted as 31a', being shown. Also shown are stops 135d, 135e in guide channels 135a, 135b. The engagement members extend inwardly from said surface toward the longitudinal axis. Of course, as illustrated in FIGS. 7-12, the lever arm comprises the features necessary to set the the first and second radial distances, but separate lever arms can also be provided, each comprising one engagement member or guide, so that exchanging the first and second lever arms changes the radial distance.

Additional Examples and Variations of the Foregoing Embodiments

Item 1. An endoscope for visually inspecting inaccessible places such as human body cavities, the endoscope comprising an insertion tube extending to a bending section having with a distal end fixed to a distal tip part including a camera connected with one or more data and/or power cables running through the bending section and insertion tube, and at least one steering wire connected with the distal end of the bending section and operable to cause bending of the bending section, the endoscope having a handle comprising:
 a fulcrum with a fulcrum axis, and
 a control lever including a lever body attached to the fulcrum and rotatable about the fulcrum axis, a lever grip having a gripping surface configured for frictionally engaging a finger of an operator, and a lever arm attaching the lever grip to the lever body, the lever body being configured to be connected with the at least one steering wire so that rotation of the control lever about the fulcrum causes tensioning of the at least one steering wire to effect bending of the bending section, the control lever being adjustable between a first and a second configuration, wherein:
 in the first configuration, the gripping surface of the lever grip is distanced from the fulcrum axis at a first radial distance via the lever body and lever arm, and
 in the second configuration, the gripping surface of the lever grip is distanced from the fulcrum axis at a second radial distance via the lever body and lever arm, wherein the second radial distance is different from the first radial distance.

Item 2. An endoscope according to item 1, wherein the lever body is configured for receiving the lever arm, wherein the control lever comprises a first guide member, a first engagement member, and preferably a second engagement member, wherein the guide member forms part of either the lever body or the lever arm and the engagement member(s) form part of the other one of the lever body and the lever arm, the engagement member(s) being configured for engaging with the first guide member so that, when the lever body receives the lever arm in the first configuration, the first engagement member is in engagement with the guide member to position the gripping surface of the lever grip at the first radial distance from the fulcrum axis, and preferably so that, when the lever body receives the lever arm in the second configuration, the second engagement member is in engagement with the guide member to position the gripping surface of the lever grip at the second radial distance from the fulcrum axis.

Item 3. An endoscope according to any one of the previous items, wherein the lever arm longitudinally extends along its longitudinal axis being perpendicular to the fulcrum axis, and the lever arm is rotatable about the longitudinal axis and configured so that rotation of the lever arm about its longitudinal axis causes the control lever to move between the first configuration and the second configuration.

Item 4. An endoscope according to item 3, wherein the control lever is configured so that rotation of the lever arm about the longitudinal axis in a first direction causes the control lever to move from the first configuration to the second configuration, and/or wherein the control lever is configured so that rotation of the lever arm about the longitudinal axis in a second direction opposite to the first direction causes the control lever to move from the second configuration to the first configuration.

Item 5. An endoscope according to item 4, wherein a 180 degree rotation of the lever arm about the longitudinal axis in the first direction causes the control lever to move from the first to the second configuration, and/or a 180 degree rotation of the lever arm about the longitudinal axis in the second direction causes the control lever to move from the second to the first configuration.

Item 6. An endoscope according to any one of the previous items, wherein the lever arm of the control lever is telescopically extendable so that a radial force relative to the fulcrum axis on the lever grip causes the control lever to move between the first configuration and the second configuration.

Item 7. An endoscope according to any one of the previous items, wherein the control lever comprises a locking mechanism, optionally a fixing snap fit, configured for preventing the lever arm from being removed from the lever body.

Item 8. An endoscope according to any one of the previous items further comprising:
- a bending section having a proximal end and a distal end fixed to the distal tip part,
- an insertion tube extending from the endoscope handle to the proximal end of the bending section,
- a distal tip part including a camera,
- one or more cables running through the bending section and insertion tube and connecting the camera with the endoscope handle, and
- at least one steering wire connecting the lever body with the distal end of the bending section so that rotation of control lever about the fulcrum axis causes bending of the bending section.

Item 9. A kit of parts for an endoscope for visually inspecting inaccessible places such as human body cavities, the kit of parts comprising:
- an endoscope including a handle comprising a fulcrum with a fulcrum axis, and a lever body attached to the fulcrum and rotatable about the fulcrum axis, the lever body being configured to be connected with at least one steering wire of the endoscope and being configured for receiving a lever arm,
- a first lever part comprising a first lever grip having a first gripping surface configured for frictionally engaging a finger of an operator, and a first lever arm configured for attaching the first lever grip to the lever body of the endoscope handle to form a first control lever, wherein rotation of the first lever grip of the first control lever about the fulcrum causes a tensioning force on the at least one steering wire to effect bending of the bending section, and
- a second lever part comprising a second lever grip having a second gripping surface configured for frictionally engaging a finger of an operator, and a second lever arm configured for attaching the second lever grip to the lever body of the endoscope handle to form a second control lever, wherein rotation of the second lever grip of the second control lever about the fulcrum causes a tensioning force on the at least one steering wire to effect bending of the bending section,
- wherein the first and second lever parts are exchangeable so that the first gripping surface of the first control lever is positioned at a first radial distance from the fulcrum axis when the first lever arm is attached to the lever body, and the second gripping surface of the second control lever is positioned at a second radial distance from the fulcrum axis when the second lever arm is attached to the lever body, the second distance being different from the first distance.

Item 10. A kit of parts according to item 9, wherein the first lever arm and/or the second lever arm is configured to be detachable from the lever body of the control lever.

Item 11. A kit of parts according to items 9-10, wherein the first lever arm and/or the second lever arm is configured to attach to and/or detach from the lever body via a snap fit.

Item 12. A kit of parts according to any one of items 9-11, wherein the endoscope handle comprises a locking mechanism having a lock state, a release state, and a locking member, wherein, in the lock state, the locking member is engaged with the first lever arm or second lever arm to prevent detachment of the first lever arm or second lever arm, and wherein, in the release state, the locking member is disengaged from the first lever arm or second lever arm to enable removal of the first lever arm or second lever arm from the lever body.

Item 13. A kit of parts according to item 12, wherein the locking mechanism is biased towards the lock state when the first lever arm or the second lever arm is received by the lever body, and wherein the locking mechanism comprises an actuator, which is configured for bringing the locking mechanism from the lock state to the release state when the actuator is actuated by the operator.

Item 14. A kit of parts according to any one of items 9-13, wherein the endoscope comprises:
- a bending section having a proximal end and a distal end fixed to the distal tip part,
- an insertion tube attaching the endoscope handle to the proximal end of the bending section,
- a distal tip part including a camera, and
- at least one steering wire connecting the body lever with the distal end of the bending section so that rotation of control lever about the fulcrum cause bending of the bending section.

Item 15. An endoscope system for visually inspecting inaccessible places, such as human body cavities, the endoscope system comprising an endoscope according to items 1-8 or a kit of parts according to any one of items 9-14, and a monitor, wherein the endoscope is connectable to the monitor, and the monitor is configured for displaying an image captured by the camera of the endoscope.

LIST OF REFERENCES

The following is a list of reference numerals used throughout this disclosure. In case of any doubt, the reference numerals of the following list apply.

1 endoscope
11 monitor
12 cable socket
13 monitor cable
20 handle
21 handle housing
22 top housing half
23 bottom housing half
24 fulcrum
25 fulcrum axis
26 block
27 working channel opening
30 control lever
31 lever body
31a opening
31b first guide
31c second guide
32 shaft
33a upper snap-fit ledge
33b lower snap-fit ledge
34 lever arm
34a longitudinal axis
35a first engagement member 35b second engagement member
36a first snap-fit cantilever
36b second snap-fit cantilever
36c snap-fit protrusion
37 lever grip
38 gripping surface
39a first radial distance
39b second radial distance
40 insertion tube
41 exterior tubular surface
50 bending section
51 proximal end
52 sleeve
60 first steering wire
61 first sheath
62 second steering wire
63 second sheath
70 distal tip part

I claim:

1. An endoscope for visually inspecting human body cavities, the endoscope comprising:
   a distal tip including a camera;
   one or more data and/or power cables;
   a bending section;
   an insertion tube extending to the bending section having a distal end fixed to the distal tip with the camera connected with the one or more data and/or power cables which run through the bending section and the insertion tube;
   at least one steering wire connected with the distal end of the bending section and operable to cause bending of the bending section; and
   a handle comprising:
      a fulcrum with a fulcrum axis, and
      a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
   wherein in the first configuration, the control lever is rotatable about the fulcrum axis and the gripping surface of the lever grip is distanced from the fulcrum axis at a first, predetermined, radial distance via the lever body and lever arm, and
   wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance,
   wherein the lever body is configured for receiving the lever arm, wherein the control lever comprises a first guide member, and a first engagement member, wherein the first guide member forms part of either the lever body or the lever arm and the first engagement member forms part of the other one of the lever body and the lever arm, the first engagement member being configured for engaging with the first guide member so that, when the lever body receives the lever arm in the first configuration, the first engagement member is in engagement with the first guide member to position the gripping surface of the lever grip at the first radial distance from the fulcrum axis, and
   wherein the control lever comprises a second engagement member, and wherein when the lever body receives the lever arm in the second configuration, the second engagement member is in engagement with the first guide member to position the gripping surface of the lever grip at the second radial distance from the fulcrum axis.

2. The endoscope of claim 1, wherein the lever arm longitudinally extends along its longitudinal axis being perpendicular to the fulcrum axis, and the lever arm is rotatable about the longitudinal axis and configured so that rotation of the lever arm about its longitudinal axis causes the control lever to move between the first configuration and the second configuration.

3. The endoscope of claim 1, wherein the lever arm of the control lever is axially extendable so that a radial force relative to the fulcrum axis on the lever grip causes the control lever to move between the first configuration and the second configuration.

4. The endoscope of claim 1, wherein the control lever comprises a locking mechanism configured for preventing the lever arm from being removed from the lever body.

5. The endoscope of claim 4, wherein the locking mechanism comprises a fixing snap fit.

6. An endoscope for visually inspecting body cavities, the endoscope comprising:
   a bending section;
   a camera;
   a distal tip part fixed to and extending from the bending section, the distal tip part including the camera;
   an insertion tube extending to the bending section, the camera connected with one or more data and/or power cables running through the bending section and insertion tube;
   at least one steering wire connected with the distal end of the bending section and operable to cause bending of the bending section; and
   a handle comprising:
      a fulcrum with a fulcrum axis, and
      a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
   wherein in the first configuration, the control lever is rotatable about the fulcrum axis and the gripping surface of the lever grip is distanced from the fulcrum axis at a first, predetermined, radial distance via the lever body and lever arm,
   wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance,
   wherein the lever body includes an elongate opening sized and shaped to receive the lever arm, wherein the control lever comprises a first ridge and a first guide channel, wherein the first ridge forms part of either the lever body or the lever arm and the first guide channel forms part of the other of the lever body or the lever arm, and wherein the first ridge is sized and shaped to slide in the first guide channel, and wherein the control lever further comprises a second guide channel and a second ridge, wherein the second guide channel forms part of either the lever body or the lever arm and the second ridge forms part of the other of the lever body or the lever arm, wherein the lever arm can be inserted into the elongate opening in the first configuration, in which the first ridge slides in the first guide channel and the second ridge slides in the second guide channel, and in the second configuration, in which the first ridge slides in the second guide channel and the second ridge slides in the first guide channel.

7. An endoscope for visually inspecting human body cavities, the endoscope comprising:
a distal tip including a camera;
one or more data and/or power cables;
a bending section;
an insertion tube extending to the bending section having a distal end fixed to the distal tip with the camera connected with the one or more data and/or power cables which run through the bending section and the insertion tube;
at least one steering wire connected with the distal end of the bending section and operable to cause bending of the bending section; and
a handle comprising:
a fulcrum with a fulcrum axis, and
a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
wherein in the first configuration, the control lever is rotatable about the fulcrum axis and the gripping surface of the lever grip is distanced from the fulcrum axis at a first, predetermined, radial distance via the lever body and lever arm, and
wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance,
wherein the lever body includes an elongate opening sized and shaped to receive the lever arm, wherein the control lever comprises a first ridge and a first guide channel, wherein the first ridge forms part of either the lever body or the lever arm and the first guide channel forms part of the other of the lever body or the lever arm, and wherein the first ridge is sized and shaped to slide in the first guide channel, and
wherein the lever arm is a first lever arm and the lever grip is a first lever grip, further comprising a second lever arm exchangeable with the first lever arm and having a second lever grip, wherein the second lever arm comprises a second guide channel and/or a second ridge, wherein in the first configuration the first lever arm can be inserted into the elongate opening with the first ridge sliding in the first guide channel, and wherein in the second configuration the second lever arm can be inserted into the elongate opening with the second ridge sliding in the first guide channel or the first ridge sliding in the second guide channel.

8. An endoscope for visually inspecting body cavities, the endoscope comprising:
a bending section;
a camera;
a distal tip part fixed to and extending from the bending section, the distal tip part including the camera;
an insertion tube extending to the bending section, the camera connected with one or more data and/or power cables running through the bending section and insertion tube;
at least one steering wire connected with the distal end of the bending section and operable to cause bending of the bending section; and
a handle comprising:
a fulcrum with a fulcrum axis, and
a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
wherein in the first configuration, the control lever is rotatable about the fulcrum axis and the gripping surface of the lever grip is distanced from the fulcrum axis at a first, predetermined, radial distance via the lever body and lever arm,
wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance,
wherein the lever arm longitudinally extends along its longitudinal axis being perpendicular to the fulcrum axis, and the lever arm is rotatable about the longitudinal axis and configured so that rotation of the lever arm about its longitudinal axis causes the control lever to move between the first configuration and the second configuration, and
wherein the control lever is configured so that rotation of the lever arm about the longitudinal axis in a first direction causes the control lever to move from the first configuration to the second configuration, and/or wherein the control lever is configured so that rotation of the lever arm about the longitudinal axis in a second direction opposite to the first direction causes the control lever to move from the second configuration to the first configuration.

9. The endoscope of claim 8, wherein a 180 degree rotation of the lever arm about the longitudinal axis in the first direction causes the control lever to move from the first to the second configuration, and/or a 180 degree rotation of the lever arm about the longitudinal axis in the second direction causes the control lever to move from the second to the first configuration.

10. An endoscope for visually inspecting human body cavities, the endoscope comprising:
 a distal tip including a camera;
 one or more data and/or power cables;
 a bending section;
 an insertion tube extending to the bending section having a distal end fixed to the distal tip with the camera connected with the one or more data and/or power cables which run through the bending section and the insertion tube;
 at least one steering wire connected with the distal end of the bending section and operable to cause bending of the bending section; and
 a handle comprising:
  a fulcrum with a fulcrum axis, and
  a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
 wherein in the first configuration, the control lever is rotatable about the fulcrum axis and the gripping surface of the lever grip is distanced from the fulcrum axis at a first, predetermined, radial distance via the lever body and lever arm, and
 wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance,
 wherein the lever arm is a first lever arm and the lever grip is a first lever grip, the endoscope further comprising:
 a second lever arm exchangeable with the first lever arm and having a second lever grip,
 wherein the lever body includes an elongate opening sized and shaped to receive the first or the second lever arm, wherein the control lever comprises a first ridge and a first guide channel,
 wherein the first ridge forms part of either the lever body or the first lever arm and the first guide channel forms part of the other of the lever body or the first lever arm, and wherein the first ridge is sized and shaped to slide in the first guide channel,
 wherein the second lever arm comprises a second guide channel and/or a second ridge,
 wherein in the first configuration the first lever arm can be inserted into the elongate opening with the first ridge sliding in the first guide channel, and
 wherein in the second configuration the second lever arm can be inserted into the elongate opening with the second ridge sliding in the first guide channel or the first ridge sliding in the second guide channel.

11. The endoscope of claim 10, wherein the first lever arm and the second lever arm are sized and structured to removably attach to the lever body.

12. The endoscope of claim 11, wherein the first lever arm and the second lever arm are removably attachable to the lever body via a snap fit.

13. The endoscope of claim 11, wherein the handle comprises a locking mechanism having a lock state, a release state, and a locking member, wherein, in the lock state, the locking member is engaged with the first lever arm or the second lever arm to prevent detachment of the first lever arm or the second lever arm, and wherein, in the release state, the locking member is disengaged from the first lever arm and the second lever arm to enable removal of the first lever arm or the second lever arm from the lever body.

14. The endoscope of claim 13, wherein the locking mechanism is biased towards the lock state when the first lever arm or the second lever arm is received by the lever body, and wherein the locking mechanism comprises an actuator, which is configured for bringing the locking mechanism from the lock state to the release state when the actuator is actuated by the operator.

15. An endoscope system for visually inspecting inaccessible places, the endoscope system comprising the endoscope according to claim 1 and a monitor, wherein the endoscope is connectable to the monitor, and the monitor is configured for displaying an image captured by the camera of the endoscope.

16. An endoscope for visually inspecting human body cavities, the endoscope comprising:
 a distal tip including a camera;
 one or more data and/or power cables;
 a bending section;
 an insertion tube extending to the bending section having a distal end fixed to the distal tip with the camera connected with the one or more data and/or power cables which run through the bending section and the insertion tube;
 at least one steering wire connected with the distal end of the bending section and operable to cause bending of the bending section; and
 a handle comprising:
  a fulcrum with a fulcrum axis, and
  a control lever including a lever arm, a lever grip, and a lever body attached to the fulcrum and rotatable about the fulcrum axis, the lever grip having a gripping surface configured for frictionally engaging a finger of an operator, and the lever arm attaching the lever grip to the lever body, the lever body connected with the at least one steering wire so that rotation of the control lever about the fulcrum causes tensioning of the at least one steering wire to effect bending of the bending section, the control lever being adjustable between a first and a second configuration,
 wherein in the first configuration, the control lever is rotatable about the fulcrum axis and the gripping surface of the lever grip is distanced from the fulcrum axis at a first, predetermined, radial distance via the lever body and lever arm, and
 wherein in the second configuration, the control lever is rotatable about the fulcrum axis and the gripping surface of the lever grip is distanced from the fulcrum axis at a second, predetermined, radial distance via the lever body and lever arm, wherein the second radial distance is different from the first radial distance, and
 wherein the lever body includes an elongate opening sized and shaped to receive the lever arm, wherein the control lever comprises a first ridge, a second ridge and a first guide channel, wherein the first ridge and the second ridge form part of either the lever body or the lever arm and the first guide channel forms part of the other of the lever body or the lever arm, and wherein the first ridge and the second ridge are sized and shaped to slide in the first guide channel in, respectively, the first and the second configuration.

\* \* \* \* \*

UNITED STATES PATENT AND TRADEMARK OFFICE
CERTIFICATE OF CORRECTION

| | |
|---|---|
| PATENT NO. | : 11,324,394 B2 |
| APPLICATION NO. | : 17/361102 |
| DATED | : May 10, 2022 |
| INVENTOR(S) | : Jesper Domino Rask |

It is certified that error appears in the above-identified patent and that said Letters Patent is hereby corrected as shown below:

On the Title Page

In Item (30) "Foreign Application Priority Data" change "Sep. 20, 2020 (DK)" to --Sep. 15, 2020 (DK)--

Signed and Sealed this
Fifteenth Day of November, 2022

Katherine Kelly Vidal
*Director of the United States Patent and Trademark Office*